US00PP25723P3

(12) United States Plant Patent
Egger

(10) Patent No.: US PP25,723 P3
(45) Date of Patent: Jul. 14, 2015

(54) ×*HEUCHERELLA* PLANT NAMED 'TWILIGHT'

(50) Latin Name: ×*Heucherella* hybrid
Varietal Denomination: Twilight

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 189 days.

(21) Appl. No.: 13/987,662

(22) Filed: Aug. 20, 2013

(65) Prior Publication Data

US 2015/0059036 P1 Feb. 26, 2015

(51) Int. Cl.
*A01H 5/12* (2006.01)

(52) U.S. Cl.
USPC ..... Plt./441

(58) Field of Classification Search
USPC ..... Plt./441
See application file for complete search history.

*Primary Examiner* — June Hwu
(74) *Attorney, Agent, or Firm* — Klarquist Sparkman, LLP

(57) ABSTRACT

A new and distinct ×*Heucherella* plant substantially as shown and described, characterized by large, rose plum to silver leaves with prominent dark veins, attractive inflorescences with white flowers in the spring, a large mounding plant habit, grows equally well in full sun or filtered shade in the Pacific Northwest, and excellent vigor.

1 Drawing Sheet

Botanical denomination: ×*Heucherella* hybrid.
Variety designation: 'Twilight'.

BACKGROUND OF THE INVENTION

The present invention relates to a new and distinct cultivar of ×*Heucherella* and given the cultivar name of 'Twilight'. ×*Heucherella* is in the family Saxifragaceae. ×*Heucherella* 'Twilight' originated from a controlled cross between *Heuchera* 'Midnight Bayou', U.S. Plant Pat. No. 21,858, as the seed parent, and massed selected proprietary *Tiarella*, as the pollen parent.

Compared to the seed parent *Heuchera* 'Midnight Bayou', the new variety has smaller leaves that are rosy silver to silver rather than purple to rose-purple.

Compared to the *Tiarella* parent, the new variety has leaves that are dark and silvered rather than green.

Compared to the closest variety ×*Heucherella* 'Infinity' PPAF, the new cultivar has leaves that are less cut and a habit that is neater, with fewer and shorter inflorescences. The new cultivar is more silvered.

This new ×*Heucherella* is distinguished by:

1. large, rose plum to silver leaves with prominent dark veins,
2. attractive short inflorescences with white flowers in the spring,
3. a large mounding plant habit,
4. grows equally well in full sun or filtered shade in the Pacific Northwest, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one and a half year old ×*Heucherella* 'Twilight' in bloom in early May, growing in the ground in full sun in the garden in Canby, Oreg.

FIG. 2 shows the same plant with summer foliage color in June.

DETAILED PLANT DESCRIPTION

The following is a detailed description of the new ×*Heucherella* cultivar based on observations of a one and a half year old specimens growing in the ground in the garden in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart,* $5^{th}$ edition.

Plant:

*Form.*—Basal rosette, herbaceous perennial.
*Hardiness.*—USDA Zone 4 to 9.
*Size.*—30 cm tall from top of the foliage to the ground and 60 cm wide.
*Habit.*—Mounding.
*Vigor.*—Excellent.
*Roots.*—Fibrous, freely branching, fine, and white in color.

Leaf:

*Type.*—Simple.
*Arrangement.*—Rosette.

*Shape.*—Broadly ovate.
*Lobing/division.*—Palmately 5 lobed, lobes shallow.
*Venation.*—Palmate.
*Margins.*—Crenate.
*Apex.*—Mucronulate.
*Base.*—Cordate, overlapping slightly.
*Blade size.*—Grows to 11 cm long and 10 cm wide.
*Surface texture.*—Both surfaces glandular.
*Petiole description.*—Grows to 23 cm long and 3 mm wide, glandular hairs, Greyed Purple 187A.
*Leaf color.*—Spring topside, closest to Greyed Purple N187B with veins Black 202A, bottom side Purple 79A; topside summer maturing closest to Grey 201B, with veins Black 202A, bottom side Greyed Purple 187A; fall and winter topside between Grey 202C and Greyed Green189C with veins Greyed Purple N186A, bottom side Greyed Purple 187A.

Inflorescence:
*Size.*—2.5 cm wide and 11.5 cm long.
*Type.*—Raceme.
*Number of flowers per raceme.*—About 50.
*Number of racemes.*—About 20.
*Peduncle.*—Grows to 43 cm tall, 3 mm wide at base, Grey Brown N199B, glandular hairs, 1 to 2 cauline leaves (petiolate, blade grows to 4 cm long and 3.5 cm wide, both sides glandular, ovate, tip acute and mucronulate, base truncate, margins 3 lobed, serrate and crenate, topside closest to Black 202A, bottom side Purple N77C).
*Pedicel.*—Grows to 4 mm long, with glandular hairs, Grey Brown N199A.
*Bloom period.*—May to June in Canby, Oreg.

Flower bud:
*Size.*—2 mm wide and 4 mm long.
*Description.*—Glandular puberulent, ovoid.
*Color.*—White N155D.

Flower:
*Type.*—Perfect.
*Shape.*—Campanulate.
*Size.*—5 mm deep and 6 mm wide.
*Petal description.*—5 in number, oblanceolate, 4 mm long and 1 mm wide, tip acuminate, base attenuate, margin entire, glabrous on both sides, White NN155D on both sides.
*Calyx description.*—3 mm deep and 3.5 mm wide, with 5 lobes, divided ½ way to the base, campanulate, glandular hairs on outside, glabrous inside, tip obtuse, margin entire, White NN155C on both sides.
*Stamen description.*—10 in number, filaments 3 mm long, White NN155D, anthers sterile, less than 1 mm, Greyed Yellow 161D.
*Pistil description.*—One central two beaked pistil, 4.5 mm long, White NN155C.
*Fragrance.*—None.
*Lastingness.*—Each raceme blooms for about 2 weeks on the plant.
*Flower attitude*.—Outwards to down-facing.
*Flowering stem attitude*.—Upright.

Fruit and seed: None.

Disease and pest tolerance: The new cultivar is typical to the genus. No known resistances to pests or diseases. No problems have been found in Canby, Oreg.

I claim:

1. A new and distinct ×*Heucherella* plant as herein illustrated and described.

* * * * *

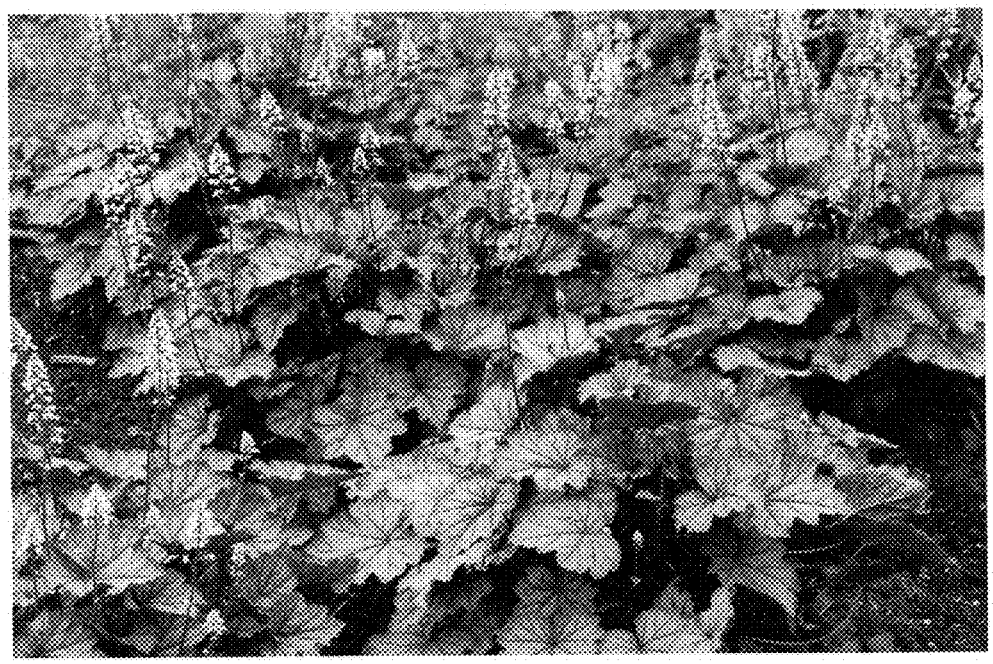
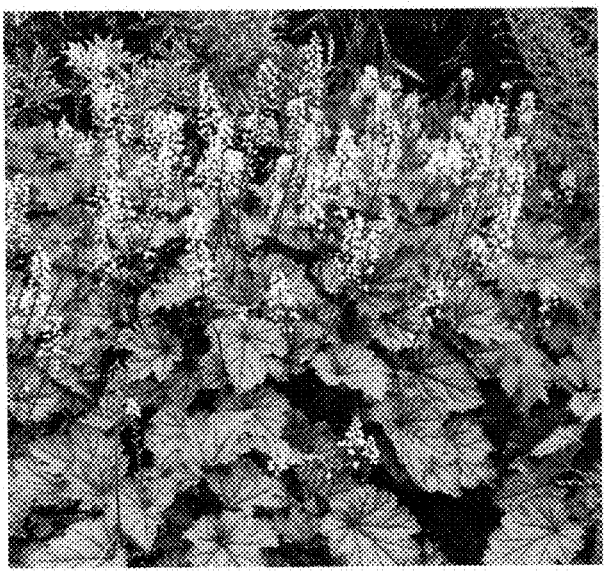
FIG. 1 above
FIG. 2 on left